US005670373A

United States Patent [19]
Kishimoto

[11] Patent Number: 5,670,373
[45] Date of Patent: *Sep. 23, 1997

[54] ANTIBODY TO HUMAN INTERLEUKIN-6 RECEPTOR

[76] Inventor: Tadamitsu Kishimoto, 5-31, Nakanocho 3-chome, Tondabayashi, Osaka, Japan

[*] Notice: The term of this patent shall not extend beyond the expiration date of Pat. No. 5,480,796.

[21] Appl. No.: 357,080

[22] Filed: Dec. 15, 1994

Related U.S. Application Data

[63] Continuation of Ser. No. 899,600, Jun. 18, 1992, abandoned, which is a continuation of Ser. No. 554,534, Jul. 20, 1990, abandoned, which is a continuation-in-part of Ser. No. 298,694, Jan. 19, 1989, Pat. No. 5,171,840.

[30] Foreign Application Priority Data

| Jan. 22, 1988 | [JP] | Japan | 63-012387 |
| Jan. 25, 1988 | [JP] | Japan | 63-012599 |
| Aug. 4, 1988 | [JP] | Japan | 63-194855 |
| Jan. 14, 1989 | [JP] | Japan | 1-007461 |
| Jul. 20, 1989 | [JP] | Japan | 1-186016 |

[51] Int. Cl.$^6$ .......................... C07K 16/00; C12P 21/04; C12N 15/00; C12N 5/00
[52] U.S. Cl. .................. 435/344; 435/70.21; 435/172.2; 435/240.27; 530/388.23; 530/387.1
[58] Field of Search ................. 435/240.27, 172.2, 435/70.21, 344; 530/388.23, 387.1

[56] References Cited

U.S. PATENT DOCUMENTS 5,171,840 12/1992 Kishimoto .......................... 530/350

FOREIGN PATENT DOCUMENTS

| 312996 | 4/1989 | European Pat. Off. |
| 325474 | 7/1989 | European Pat. Off. |
| 61-24697 | 2/1986 | Japan . |
| 61-246197 | 11/1986 | Japan . |
| 899776 | 7/1990 | Japan . |
| 899774 | 11/1990 | Japan . |

OTHER PUBLICATIONS

Maniatis et al., Molecular Cloning, pp. 188–189 and 213–246, Cold Spring Harbor Lab. (1982).
Shimamura et al. Translation of Summary document of Proceedings of the Japanese Society for Immunology, B2–66 Attempt to Prepare Monoclonal Antibodies to human BSF2/IL–6 Receptor (Dec. 6, 1988).
McClelland et al., Methods in Enzymology, vol. 147: 280–290 (1987).
Okuno et al., Exp. Hematol., 20(4): 395–400 (May 1992).
Taga et al., Cell, 58(3): 573–581 (Aug. 11, 1989).
Bataille et al., J. Clin. Invest., 84(6): 20008–2011 (Dec. 1989).
Yasukawa et al., J. Biochem., 108(4): 673–676 (Oct. 1990).
Hirano et al., Summary of Presentation of the 17TH Conference of Japan Immunology (In Japanese).
Kishimoto et al., Studies of B–Cell Growth, Differentiation and Aberrant Control (Mar. 1989) (In Japanese).

Biological Abstracts vol. 28, 1985 No. 65431.
Biological Abstracts vol. 84 No. 12 1987 No. 118862.
Nishikawa Chemical Abtracts, vol. 109 p. 193 No. 87407d Jun. 5, 1989.
Yamasaki et al., "Cloning and Expression of the Human Interleukin–6 (BSF–2/IFNβ2) Receptor", *Science*, 241:825–828 1988, Aug. 12).
Kishimoto et al., "Molecular Regulation Of B Lymphocyte Response", *Ann. Rev. Immunol.*, 6:485–512, 1988.
Hirano et al., "Human B–Cell Differentiation Factor Defined By An Anti–Peptide Antibody And Its Possible Role In Autoantibody Production", *Proc. Natl. Acad. Sci. USA*, 84:228–231.
Taga et al., "Receptors For B Cell Simulatory Factor 2 Quantitation, Specificity, Distribution, and Regulation Of Their Expression", *J. Exp. Med.*, 166:967–981, 1987.
Hirata et al., J. Immunol. 143, 2900–2906, (1989 Nov. 1).
Chemical Abstract vol.109, 1988, p. 546, No. 71738b.
Devereux et al., the Program Manual for the Sequence Analysis Software Package, Genetics Computer Group, versions, 1987.
Lerner, Nature 299, 592–6, 1982.
HIBI et al., Translation of *Proc. Jpn. Soc. Immuno.*, vol. II (Oct. 20, 1989).
Palfreyman et al., J Immunol. Mtds. 75: 383–393, 1984.
Biological Abstract vol. 89, Jan. 1990, No. 15076.
Chemical Abstract vol.110, No.23, Jun. 1989, No.210580 e.
Chemical Abstract vol.111, No.1, Jul. 1989, No. 5589 u.
May et al., "Anti–β–Interferon Antibodies Inhibit The Increased Expression Of HLA–B7 mRNA In Tumor", *Sci. USA*, 83:8957–8961, Dec., 1986.
Zilberstein et al., "Structure And Expression Of cDNA And Genes For Human Interferon–beta–2, A Distinct Species Inducible By Growth–Stimulatory", *Journal*, 5:2529–2537 Jul. 22, 1986.
Hirano et al., "Complementary DNA For A Novel Human Interleukin (BSF–2) That Induces B Lymphocytes To Produce Immunoglobulin", *Nature*, 324:73–76, Nov., 1986.
Hirano et a., "Human B–Cell Differentiation Factor Defined By An Anti–Peptide Antibody And Its Possible role In Autoantibody Production", *Proc. Natl. Acad. Sci. USA*, 84:228–231 Jan., 1987.
Seed, "An LFA–3 cDNA Encodes A Phospholipid–linked Membrane Protein Homologous To Its Receptor CD2", *Nature*, 329:840–842, Oct. 29, 1987.
Messing, "New M13 Vectors For Cloning", *Methods in Enzymology*, 101:20–79, 1983.

(List continued on next page.)

*Primary Examiner*—Anthony C. Caputa
*Assistant Examiner*—Mark Navarro
*Attorney, Agent, or Firm*—Foley & Lardner

[57] ABSTRACT

Antibodies, polyclonal and monoclonal, which are capable of specifically binding to a human interleukin-6 receptor. Also included are monoclonal antibodies which competitively and non-competitively inhibit human interleukin-6, and a method of producing hybridomas of the said monoclonal antibodies capable of specifically binding to a human interleukin-6 receptor.

13 Claims, 5 Drawing Sheets

OTHER PUBLICATIONS

Tyndall et al., "A Region Of The Polyoma Virus Genome Between The Replication Origin And Late Protein" *Research*, 9:6231–6250 Nov. 23, 1981.

Nakajima–Iijima et al., "Molecular Structure Of The Human Cytoplasmic β–actin Gene: Interspecies Homology Of Sequences In The Introns", *Proc. Natl. Acad. Sci. USA*, 82:6133–6137 Sep. 1985.

Ellis et al., "Replacement Of Insulin Receptor Tyrosine Residues 1162 And 1163 Compromises Insulin–Stimulated Kinase Activity And Uptake of 2–Deoxyglucose", *Cell*, 45:721–732, Jun. 6, 1986.

Wigler et a., "Biochemical Transfer Of Single–Copy Eucaryotic Genes Using Total Cellular DNA As Donor", *Cell*, 14:725–731 Jul. 1978.

Chu et al., "SV40 DNA Transfection Of Cells In Suspension: Analysis Of The Efficiency Of Transcription And Translation Of T–Antigen", *Gene*, 13:197–202 1981.

Fujii et al. J. Immunol. 137: 1552–1556, 1986.

Hirata et al. J Immunology 143(9) : 2900–2906 Nov. 1989.

Yamasaki et al. Science 241:825–828 Aug. 1988.

Mäkelä et al. pp. 3.1–3.13 in Weir et al., *Handbook of Experimental Immunology* vol. 1 , 1986 , Blackwell.

Milstein , pp. 107.1–107.12 in Weir et al. *Handbook pf Experimental Immunology* vol. 4, 1986, Blackwell.

Fig. I(A)
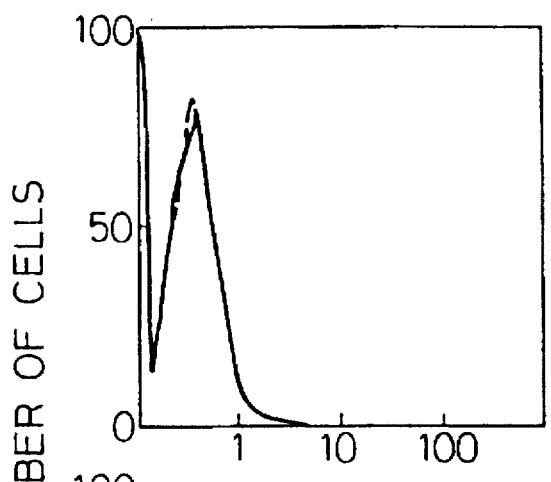
Fig. I(B)
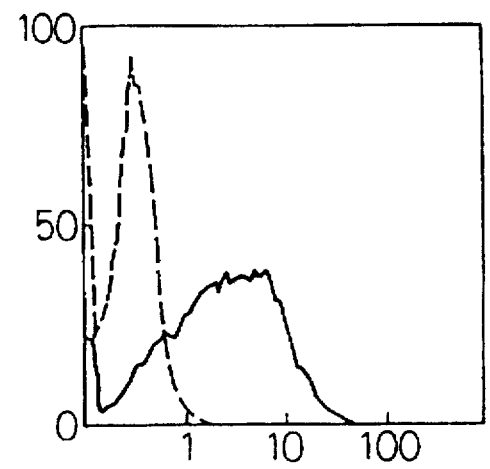
Fig. I(C)
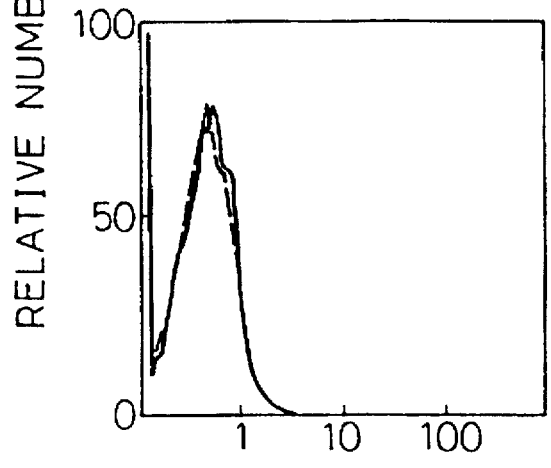
Fig. I(D)
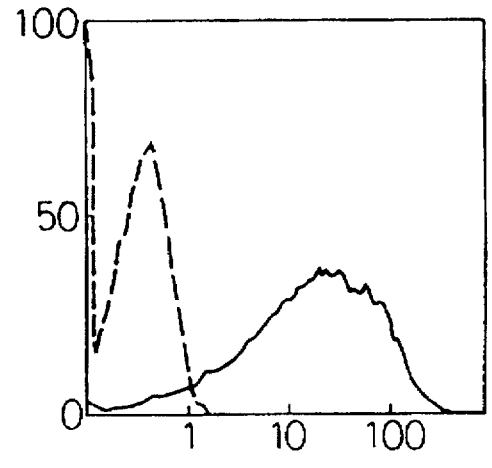
INTENCITY OF FLUORESCENCE Fig. 6(A)
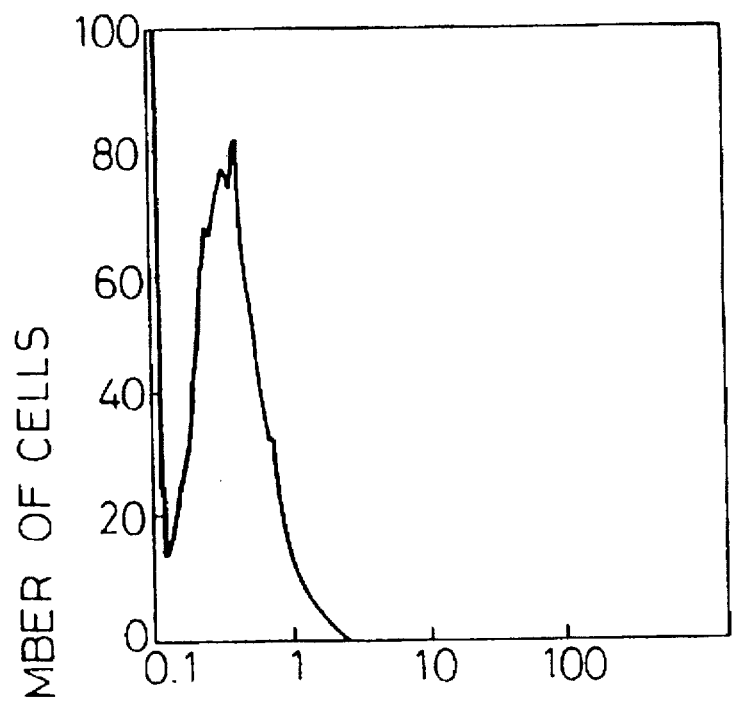
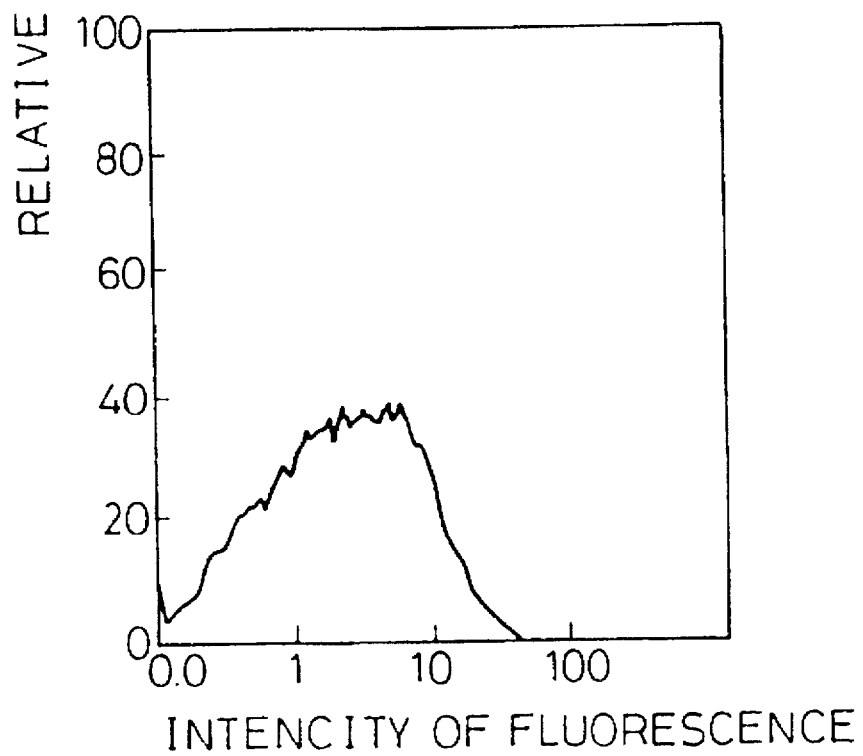
INTENCITY OF FLUORESCENCE
Fig. 6(B)

ANTIBODY TO HUMAN INTERLEUKIN-6 RECEPTOR

This application is a continuation application of application Ser. No. 07/899,600, filed Jun. 18, 1992, now abandoned, which is a continuation application of Ser. No. 07/554,534, filed on Jul. 20, 1990, now abandoned, which is a continuation-in-part application of Ser. No. 07/298,694, filed Jan. 19, 1989, now issued as U.S. Pat. No. 5,171,840.

BACKGROUND OF THE INVENTION (1) Field of the Invention

The present invention relates to antibodies which specifically bind to a human IL-6 receptor, and a process for the preparation thereof.

(2) Description of the Related Art

Interleukin-6 (hereinafter abbreviated to "IL-6") is a protein having various important physiological activities and participating broadly in the proliferation and differentiation of cells. Furthermore, it is reported that an abnormal production of IL-6 is possibly a factor causing various autoimmune diseases (see Kishimoto and Hirano, Ann. Rev. Immunol., 6, page 485, 1988).

IL-6 receptors on the cell membrane, which specifically bind to IL-6, were analyzed by Taga et al., and the number on each cell and binding constant to IL-6 were reported (see J. Exp. Med., 196, page 967, 1987). Furthermore, the cDNA of human IL-6 receptor was isolated, and the primary structure thereof was reported by Yamazaki et al. (see Science, 241, page 825, 1988). IL-6 receptor which is prepared by a genetic engineering method based on these results, is expected to become a therapeutic or diagnostic agent for various immune diseases.

For a mass production and homogeneous purification of such IL-6 receptors, the development of an antibody to the IL-6 receptor as a means for promptly identifying the IL-6 receptor is required, but a monoclonal antibody capable of recognizing the IL-6 receptor has not been known.

SUMMARY OF THE INVENTION

Therefore, a primary object of the present invention is to provide various types of antibodies to IL-6 receptor.

To attain this object, the present invention provides antibodies to human interleukin-6 receptor, which is capable of binding specifically to a human interleukin-6 receptor.

Furthermore, the present invention provides a hybridoma producing a monoclonal antibody having the above-mentioned properties.

The present invention also provides a process for the preparation of the hybridoma, which comprises immunizing a mammal with a human interleukin-6 receptor antigen, obtaining immunocytes from the mammal, fusing the immunocytes with a myeloma cells, and cloning a hybridoma cell line capable of recognizing a human interleukin-6 receptor from the fused cells.

The present invention further provides a process for the preparation of an antibody to a human interleukin-6 receptor, which comprises culturing the above-mentioned hybridoma and recovering a monoclonal antibody capable of recognizing a human interleukin-6 receptor from the culture.

The present invention also provides a process for the preparation of a polyclonal antibody to a human interleukin-6 receptor, which comprises immunizing a mammal with a human interleukin-6 receptor antigen and recovering a polyclonal antibody capable of recognizing a human interleukin-6 receptor from the immunized mammal.

BRIEF DESCRIPTION OF THE DRAWINGS

FIG. 1A–D shows the reactivity of a T-cell line Jurkat in which the IL-6 receptor is not expressed [curves (a) and (c)], or a Jurkat in which an IL-6 receptor cDNA-containing vector is introduced and the IL-6 receptor is durably expressed [curves (b) and (d)], with the culture supernatant of MT18 [solid lines in curves (a) and (b)] or the culture supernatant of PM1 [solid lines in curves (c) and (d)]. The dotted lines show the results for the cells not treated with the culture supernatant;

FIG. 6A and B is a cell distribution diagram showing that the MT18 antibody binds only IL-6 receptor-producing cells.

DESCRIPTION OF THE PREFERRED EMBODIMENTS

Figure 2:
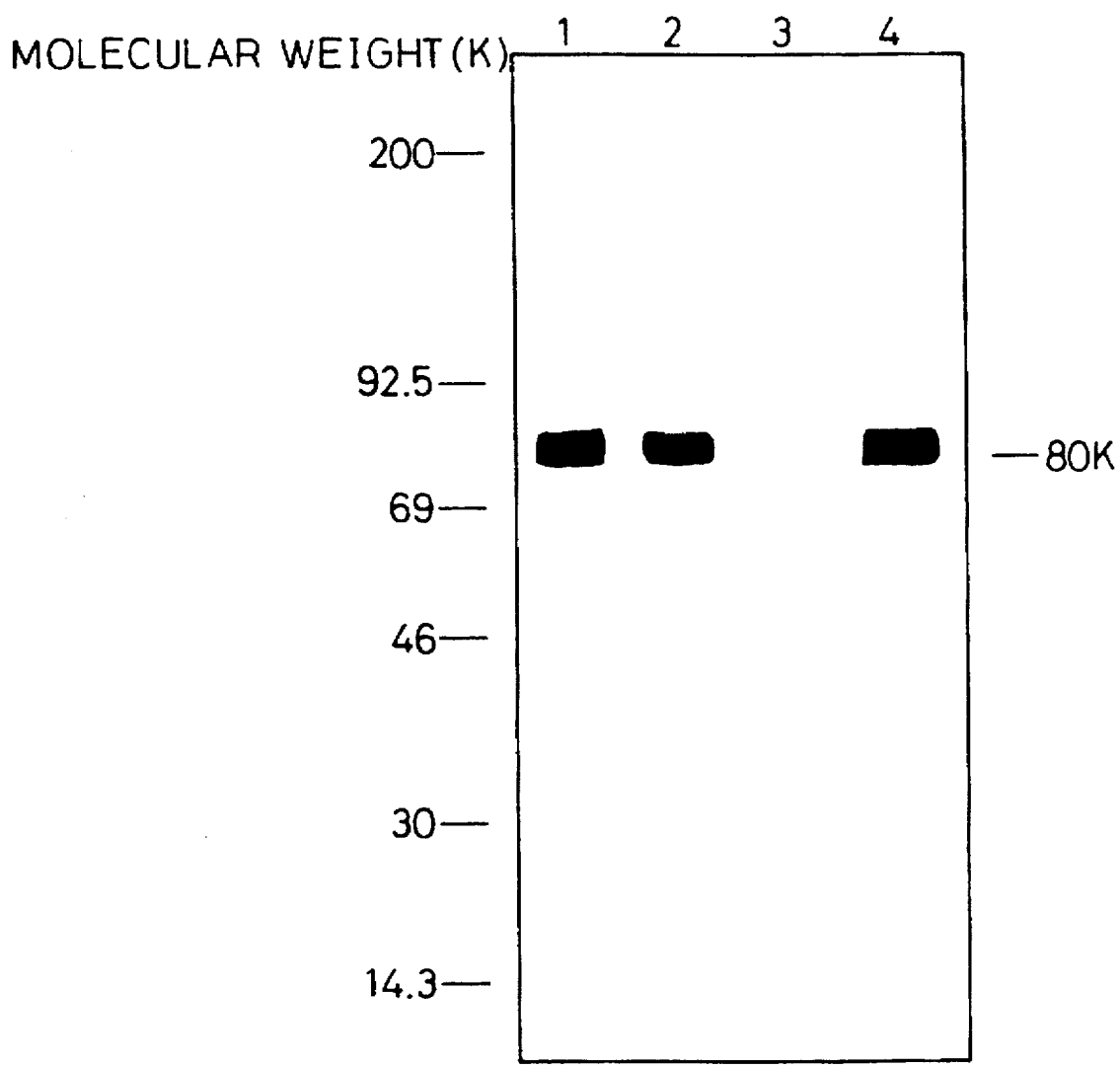
FIG. 2 shows the results obtained by solubilizing internally labelled U266 cells, effecting immunoprecipitation with an MT18 monoclonal antibody (lane 1), PM1 monoclonal antibody (lane 2), rabbit immunoglobulin (lane 3) or anti-peptide polyclonal antibody of Example 3 (lane 4), and subjecting same to SDS-polyacrylamide gel electrophoresis and autoradiography.

Antibodies of the present invention specifically recognize a human IL-6 receptor, and include monoclonal and polyclonal antibodies. The monoclonal antibodies include antibodies competitively inhibiting the binding of human IL-6 to a human IL-6 receptor and antibodies not competitively inhibiting this binding. The former antibodies, include, for example, PM1 monoclonal antibody produced by the hybridoma PM1 of the present invention, and the latter antibodies include, for example, MT18 monoclonal antibody produced by the hybridoma MT18.

As an immunogen used for the preparation of the antibodies of the present invention, there can be mentioned animal cells having human IL-6 receptors expressed on the surface thereof. Such animal cells include a human-derived cell line producing human IL-6 receptor, for example, human myeloma cell line U266, and host cells transformed with DNA coding for human IL-6 receptor, for example, animal cell line such as mouse T-cells transformed with a plasmid comprising cDNA coding for human IL-6 receptor. Nevertheless, these cell lines are not regarded as an effective antigen, because the quantity of the IL-6 receptor expressed on the cell surface is small.

Nevertheless, even though such an immunogen is used to produce an antibody, once an antibody to a human IL-6 receptor has been obtained, it is possible to prepare a more effective immunogen by using this antibody, and to prepare a variety of antibodies by using this immunogen. For example, an immunogen can be prepared by bonding an antibody to a human IL-6 receptor to an appropriate solid carrier, culturing cells producing a human IL-6 receptor, for example, the above-mentioned cells and lysing the cells, and bringing the cell lysate into contact with the above-mentioned human IL-6 receptor antibody-bonded solid carrier to adsorb and concentrate the human IL-6 receptor in the cell lysate on the carrier. The kind of solid carrier is not particularly critical, as long as the solid carrier is capable of binding the antibody and preferably has no serious influence on the growth of an animal to be immunized. For example, a Sepharose-based solid carrier, as described in the Examples hereinafter, is preferably used as the solid carrier in the present invention, because the binding of the antibody to this carrier is a simple operation and there are no influences on the growth of an animal to be immunized. Alternatively, human IL-6 receptor can be prepared according to a genetic engineering process, for example, the process disclosed in the Japanese Patent Application 89-9774, and this receptor can be used as the immunogen. Still further, an immunogen prepared by forming a peptide comprising a part of a human IL-6 receptor and attaching this peptide to a polymeric carrier for example a protein such as ovalbumin can be used. A vaccinia virus arranged so that human IL-6 receptor will be expressed after the infection also can be used as an immunogen. Any of these immunogens can be used as the immunogen for the preparation of a polyclonal antibody and for the preparation of a hybridoma.

The polyclonal antibody is prepared by immunizing a mammal such as mouse, rabbit, sheep, goat or the like with any of the above-mentioned antigens, according to conventional procedures.

Also, hybridoma can be prepared according to conventional procedures, for example, by immunizing a mammal such as a mouse with any of the above-mentioned antigens, obtaining spleen cells from this animal, fusing the cells with established myeloma cells, and then cloning a hybridoma producing a monoclonal antibody having a desired reactivity.

A monoclonal antibody is prepared by culturing the cloned hybridoma and recovering the monoclonal antibody from the culture supernatant. Alternatively, a monoclonal antibody can be prepared by intraperitoneally infecting an animal with the above-mentioned hybridoma, collecting ascites from the animal, and isolating the monoclonal antibody. The antibody in the hybridoma cell supernatant or the antibody in the ascites can be concentrated according to a conventional procedure, for example, by salting-out with ammonium sulfate, and can be purified by an affinity chromatography, for example, an affinity chromatography on an IL-6 receptor-immobillized carrier.

All of the processes for the preparation of the monoclonal antibody, the preparation of the hybridoma, the preparation of the monoclonal antibody, and the recovery and purification of the antibody can be carried out according to methods well-known in the art.

The present invention will now be described in detail with reference to the following examples, that by no means limit the scope of the invention.

EXAMPLE 1

(Preparation of Mouse Monoclonal Antibody to Human IL-6 Receptor)

For preparing a mouse monoclonal antibody to human IL-6 receptor, a mouse T-cell line having human IL-6 receptors expressed on the membrane surface was prepared as an immunogen, according to the following process. Namely, pBSF2R.236 and pSV2neo disclosed in the Japanese Patent Application No. 89-9774 were introduced into mouse T-cells CTLL-2 (ATCC, TIB214) according to a conventional method, and the screening was carried out according to a conventional method using G-418. Finally, a cell line in which about 30,000 IL-6 receptors per cell were expressed was established and named "CTBC3".

Immunization was carried out in the following manner. Namely, CTBC3 was cultured by a conventional method using PRMI1640, washed with PBS buffer 4 times, and was intraperitoneally introduced to C57BL6 mouse in a quantity of $1 \times 10^7$ cells per mouse once a week, six times as a whole.

The spleen cells from the immunized mouse were fused with myeloma cells P3U1 as a parent cell line, according to a conventional method using polyethylene glycol.

The screening was carried out in the following manner. Namely, pBSF2R.236 and pSV2neo were introduced into human T-cells JURKAT (ATCC, CRL8163) negative to the IL-6 receptor, and after screening, a cell line in which about 100,000 IL-6 receptors per cell were expressed was established and named "NJBC8". One clone of hybridoma producing an antibody which recognizes NJBC8 solubilized with NP40 and does not recognize JURKAT solubilized with NP40, was isolated and this hybridoma was named "MT18". Furthermore, the monoclonal antibody produced by this hybridoma was named "MT18 antibody". The above-mentioned hybridoma MT18 was deposited at the Fermentation Research Institute (FRI) Agency of Industrial Science and Technology 1–3 Yatabe-cho Higashi 1-chome Ibaraki Japan as FERM P-10840 on Jul. 12, 1989, and transferred to an international deposition under the Budapest Treaty as FERM BP-2999 on Jul. 10, 1990. The data of FIG. 6 shows that the MT18 antibody specifically recognizes the IL-6 receptor. In FIG. 6, curve A shows the distribution of fluorescein-stained cells, when JURKAT cells are stained with the MT18 antibody labelled with fluorescein isocyanate, and curve B shows the result when the above-mentioned NJBC8 cell is similarly treated.

EXAMPLE 2

(Preparation of Monoclonal Antibody to IL-6 Receptor)

For preparing a mouse monoclonal antibody to IL-6 receptor, human IL-6 receptors were extracted as an immunogen in the following manner.

Namely, $3 \times 10^9$ human myeloma cells of cell line U266 (IL-6 receptor-producing cells) were solubilized with 1 ml of 1% digitonin (supplied by Wako Junyaku), 10 mM triethanolamine buffer (pH 7.4), 0.15M NaCl and 1 mM PMSF (supplied by Wako Junyaku). On the other hand, MT18 antibody (Example 1), i.e., an antibody to IL-6 receptor, was attached to Sepharose 4B (supplied by Pharmacia) according to a conventional manner. The antibody-bonded carrier was mixed with a supernatant of the solubilized cells to bond the solubilized IL-6-receptor to the MT18 antibody on the carrier. Non-specifically bonded product was washed off with the above-mentioned 1% digitonin solution, and the IL-6 receptor bonded to the Sepharose 4B through the MT18 antibody was used as an immunogen for one immunization.

The immunization and the preparation of hybridoma were carried out in the following manner. A Balb/c mouse was immunized intraperitoneally with the above-mentioned immunogen four times, once a week. The spleen cells from the mouse were fused with myeloma cells P3U1 as a parent cell line, according to a conventional process using polyethylene glycol.

The screening was carried out in the following manner. First, a culture supernatant of the hybridoma was mixed with Protein G-Sepharose resin (supplied by Pharmacia), whereby immunoglobulin in the supernatant was adsorbed to the resin. On the other hand, $10^7$ U266 cells internally labelled with $^{35}$S-methionine were solubilized, and then, the IL-6-receptor was affinity-purified on the above-mentioned MT18 antibody-bonded Sepharose 4B described above, immunoprecipitated with the above-mentioned Protein G-Sepharose, and analyzed by SDS/PAGE. As a result, one clone of hybridoma producing an antibody which specifically binds to IL-6 receptor was isolated and named "PM1". The monoclonal antibody produced by this hybridoma was named "PM1 antibody".

The hybridoma PM1 was deposited at the Fermentation Research Institute (FRI) of Agency of Industrial Science and Technology in Japan as FERM-P 10839 on Jul. 12, 1989, and transferred to an international deposition under the Budapest Treaty as FERM BP-2998 on July 10, 1990.

The reactivities of the monoclonal antibodies PM1 and MT18 with the IL-6 receptor are shown in FIG. 1. Namely, the T-cell line Jurkat in which the IL-6 receptor was not expressed [curves (a) and (c) in FIG. 1] and the cell line Jukat in which cDNA of the IL-6 receptor has been introduced and the IL-6-receptor was durably expressed (curves (b) and (d)), were separately reacted with a culture supernatant of MT18 [solid lines in curves (a) and (b) in FIG. 1] or of PM1 [solid lines in curves (c) and (d)]. The reaction products were reacted with a goat anti-mouse antibody conjugated to a fluorescence dye, and the distribution of the fluorescein-stained cells relative to the fluorescein intensity was examined. For comparison, the results obtained from corresponding cells treated with neither the culture supernatant of MT18 or PM1, are indicated by dotted lines in boxes (a), (b), (c) and (d) in FIG. 1.

From these results, it was confirmed that each of the PM1 and MT18 antibodies can be bonded to the IL-6 receptor.

EXAMPLE 3

(Preparation of Polyclonal Antibody to IL-6 Receptor)

For preparing a polyclonal antibody to IL-6 receptor, a peptide: KTSMHPPYSLGQLVPC (K represents lysine, T represents threonine, S represents serine, M represents methionine, H represents histidine, F represents phenylalanine, P represents proline, Y represents tyrosine, L represents leucine, G represents glycine, Q represents glutamine, V represents valine, and C represents cysteine residue) in which a cystein residue is added to a peptide corresponding to a part of the intracellular region of an IL-6 receptor was synthesized according to a conventional method.

This synthetic peptide was attached to ovalbumin according to the process of T. Hirano et al (Proc. Natl. Acad. Sci. USA, 84, page 228, 1987). A rabbit was immunized with 0.2 mg of the product 5 times once a week. The whole serum was collected from the rabbit and subjected to affinity purification on a synthetic peptide-bounded Sepharose 4B.

The data shown in FIG. 2 indicates that the prepared polyclonal antibody can specifically recognize the IL-6 receptor. Namely, internally labelled U266 cells (IL-6 receptor-producing cells) were solubilized with a detergent, and the obtained cell lysate was immunoprecipitated with the MT18 antibody (lane 1), the PN1 antibody (lane 2), rabbit immunoglobulin (lane 3) or the anti-peptide polyclonal antibody prepared in Example 3 (lane 4) and then subjected to SDS-polyacrylamide gel electrophoresis and autoradiography. As a result, it was confirmed that each of the MT18 monoclonal antibody, the PM1 monoclonal antibody and the anti-peptide polyclonal antibody specifically recognized the IL-6 receptor.

EXAMPLE 4

(Competitive Inhibition of Bindingq of IL-6 to IL-6 Receptor by PM1 Antibody)

Labelling of IL-6 and identification of binding of IL-6 to an IL-6 receptor on cell were carried out according to the method of T. Taga et al. (see J. Exp. Med., 166, page 967, 1987). $^{125}$I-IL-6 (14,000 cpm) was reacted with $4\times10^5$ of U266 cells (IL-6 receptor-producing cells) at room temperature for 60 minutes. This reaction was carried out in the presence of unlabelled IL-6 in 100-fold excess of the number of molecules, the culture supernatant of MT18 (70% by volume) or the culture supernatant of PM1 (70% by volume). The cells were overlaid on FCS, centrifuged, and the radioactivity of the cells was measured. For comparison, a culture medium not inoculated with the cells was similarly treated.

Figure 3:
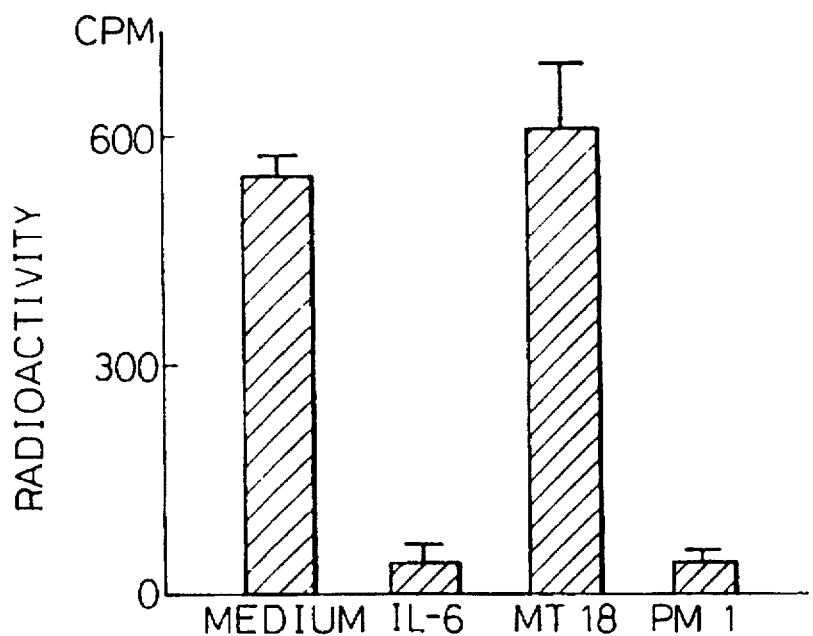
FIG. 3 is a graph showing the inhibiting effects of PM1 and MT18 antibodies on the binding of IL-6 to the IL-6 receptor according to the procedure described in Example 4.

The data of FIG. 3 indicates that the MT18 antibody does not competitively inhibit the binding of IL-6 to the IL-6 receptor while the PM1 antibody competitively inhibits this binding.

Figure 4A:
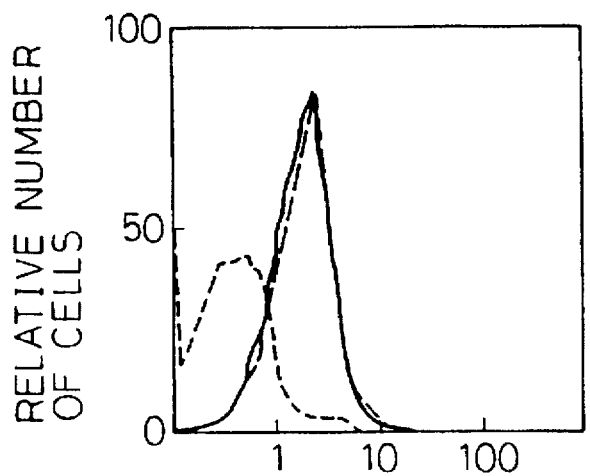
FIG. 4A–B shows the results of a comparison of the bindings of the MT18 antibody [curve (a)] and PM1 antibody [curve (b)] to U266 cells in the presence (broken line) or absence (solid line) of IL-6, and the dotted lines show the results for U266 cells treated with only IL-6.
Figure 4B:
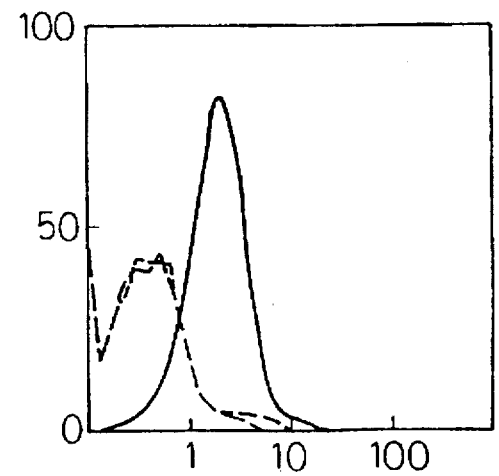

Similar results are also shown in FIG. 4. In FIG. 4, curve (a) shows the distribution of the number of cells relative to the fluorescence intensity, in which U266 cells were reacted with the culture supernatant of MT18 in the presence (broken line) or absence (solid line) of IL-6 and then stained with fluorescence-labelled anti-mouse immunoglobulin; and curve (b) shows the results when U266 cells were reacted with the culture supernatant of PN1 in the presence (broken line) or absence (solid line) of IL-6 and treated in the same manner as curve (a). It is seen that the MT18 antibody was bonded to the U266 cells whether in the presence of IL-6 or not, while the PM1 antibody was bonded to the U266 cells in the absence of IL-6 but not bonded to the U266 cells in the presence of an excess of IL-6. Accordingly, it is confirmed that the PM1 antibody is competitive with IL-6.

EXAMPLE 5

(Confirmation of Inhibition of Biological Activities of IL-6 by PM1 Antibody)

IL-6-dependent human T-cell leukemia line KT3 was cultured according to the process of S. Shimizu et al. (see Blood, 72, page 1826, 1988), and IL-6 was added at various concentrations in the presence or absence of 25% by volume of the culture supernatant of the hybridoma PM1. Culturing was conducted in a commercially available 96-well plate. The cell number was $5\times10^3$ per 100 μl in each well. After 60 hours, 0.75 μCi of tritium-labelled thymidine per well was added, and after 6 hours, the cells were collected and the incorporated radioactivity was measured.

Figure 5:
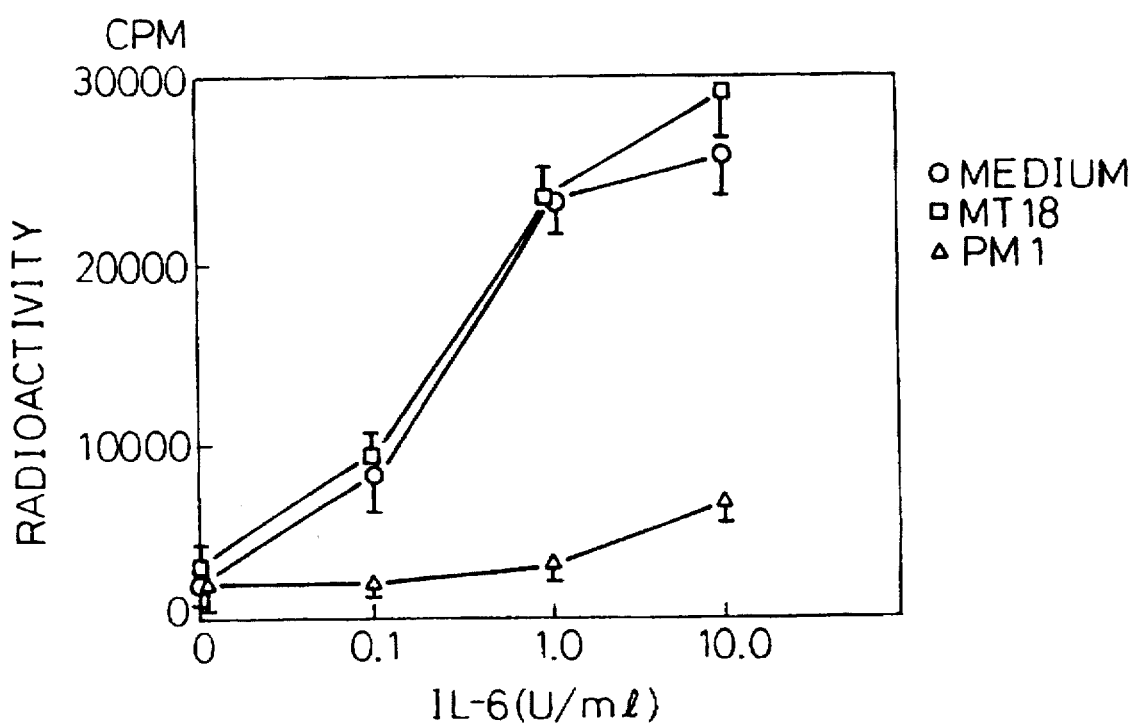
FIG. 5 shows the incorporation of tritium-labelled thymidine by KT3 cells cultured with various concentrations of IL-6, in the presence or absence of the culture supernatant of MT18 or PM1.

Data of FIG. 5 indicates that the MT18 antibody does not inhibit the biological activities of IL-6 while the PM1 antibody inhibits the biological activities of IL-6.

The polyclonal and monoclonal antibodies recognizing specifically IL-6 receptor, provided by the present invention, are useful for producing and purifying large quantities of various proteins having an IL-6 receptor activity which are expected as diagnostic or therapeutic agents.

Furthermore, the antibody provided by the present invention make it possible to analyze various properties of IL-6 receptor which is produced only in a very small amount in the natural state. This is very significant for an investigation of ontogenesis and immune mechanisms, and for a development of therapeutic and diagnostic agents based on the results thereof.

Moreover, it is considered that the antibody inhibiting biological activities of IL-6, provided by the present invention, will be applied to the development of therapeutic agents for various autoimmune diseases assumed to be caused by an abnormal production of IL-6.

EXAMPLE 6

(Preparation of Monoclonal Antibody to a Portion of IL-6 Receptor)

Balb/c mouse was intraperitonealy immunized with the antigen used in Example 3, i.e., a synthetic peptide KTSMHPPYSLGQLVPC conjugated with ovalbumin, four times once a week. Next, the spleen cells from the mouse were fused with myeloma cells using polyethylene glycol according to a conventional process.

The screening was carried out in the following manner. First, a culture supernatant of the hybridoma was mixed with Protein G-Sepharose resin (Pharmacia), whereby immunoglobulin in the supernatant was adsorbed to the resin. On the other hand, $10^7$ U266 cells internally labelled with $^{35}$S-methionine were solbilized, immunoprecipitated with the above-mentioned Protein G-Sepharose, and anloyzed by SDS/PAGE. As a result, a band of IL-6 receptor was detected. On the other hand, when the antigen peptide (KTSMHPPYSLGQLVPC) was added during the immunoprecipitation, no band was detected. As a result, one clone of hybridoma which produces an monoclonal antibody specifically recognizing a portion of intracellular region of IL-6 receptor was isolated.

I claim:

1. An isolated antibody to human interleukin-6 receptor, wherein said antibody specifically binds to said human interleukin-6 receptor.

2. An antibody according to claim 1, wherein said antibody can specifically bind to amino acid sequence KTS MHP PYS LGQ LVP of said human interleukin-6 receptor.

3. An antibody according to claim 1, wherein said antibody is monoclonal.

4. An antibody according to claim 3, wherein said antibody is polyclonal.

5. An antibody according to claim 3, wherein said antibody is produced by hybridoma MT18 (FERM BP-2999).

6. An antibody according to claim 3, wherein said antibody is produced by hybridoma PM1 (FERM BP-2998).

7. A hybridoma capable of producing a monoclonal antibody to human interleukin-6 receptor, wherein said monoclonal antibody can specifically bind to human interleukin-6 receptor.

8. A hybridoma according to claim 7, wherein said hybridoma is hybridoma MT18 (FERM BP-2999).

9. A hybridoma according to claim 7, wherein said hybridoma is hybridoma PM1 (FERM BP-2998).

10. A process for the production of a monoclonal antibody to human interleukin-6 receptor, wherein said monoclonal antibody is capable of specifically binding human interleukin-6 receptor, comprising the steps of 1) culturing hybridoma cells producing said monoclonal antibody; and 2) recovering the supernatant from said culturing step.

11. A process according to claim 10, wherein said hybridoma cells are hybridoma PM1 cells (FERM BP-2998).

12. A process according to claim 10, wherein said hybridoma cells are hybridoma MT18 cells (FERM BP-2999).

13. A process for the preparation of a polyclonal antibody directed against human interleukin-6 receptor, comprising the steps of 1) immunizing an animal with a peptide having the amino acid sequence KTS MHP PYS LGQ LVP; and 2) recovering said polyclonal antibody from said immunized animal.

\* \* \* \* \*